United States Patent [19]
Hoyt et al.

[11] Patent Number: 5,473,954
[45] Date of Patent: Dec. 12, 1995

[54] APPARATUS FOR TESTING POLYMONARY DEVICES

[75] Inventors: Mark J. Hoyt, Midvale; Jon A. Bertrand, Kearns, both of Utah

[73] Assignee: MH Custom Design & Mfg., L.C., Midvale, Utah

[21] Appl. No.: 397,712

[22] Filed: Mar. 2, 1995

Related U.S. Application Data

[63] Continuation of Ser. No. 29,615, Mar. 11, 1993, abandoned.

[51] Int. Cl.⁶ .................................................. G01M 19/00
[52] U.S. Cl. ................................................ 73/865.6; 75/37
[58] Field of Search ........................ 73/865.9, 3, 866.4, 73/865.6, 37

[56] References Cited

U.S. PATENT DOCUMENTS

| | | | |
|---|---|---|---|
| Re. 29,317 | 7/1977 | Mosley et al. | 73/866.4 |
| 3,049,812 | 8/1962 | Bovard | 73/865.6 |
| 3,420,225 | 1/1969 | Holden et al. | 73/262 X |
| 3,589,190 | 6/1971 | Jones | 73/279 |
| 4,324,127 | 4/1982 | Gazzara et al. | 73/3 |
| 4,430,893 | 2/1984 | Barkalow | 73/168 |
| 5,076,093 | 12/1991 | Jones, Jr. et al. | 73/3 |
| 5,327,774 | 7/1994 | Nguyen et al. | 73/37 |

FOREIGN PATENT DOCUMENTS

| | | | |
|---|---|---|---|
| 2344898 | 3/1975 | Germany | 73/865.6 |
| 21164 | 2/1983 | Japan | 73/865.6 |
| 11980 | 1/1959 | U.S.S.R. | 73/865.6 |
| 498526 | 1/1976 | U.S.S.R. | 73/866.4 |
| 685294 | 9/1979 | U.S.S.R. | 73/866.4 |

Primary Examiner—Thomas P. Noland
Attorney, Agent, or Firm—Bacon & Thomas

[57] ABSTRACT

An apparatus for testing pulmonary devices such as endotracheal tubes and connectors is disclosed. The apparatus forces a predetermined volume of air or gas through the pulmonary device in accordance with a preselected waveform in a first and/or second direction under conditions that simulate an in-patient use environment. The device also measures the amount of work required to force the air or gas through the device under selected conditions. In a preferred embodiment of the invention, the device produces a laminar or turbulent flow of gas.

6 Claims, 3 Drawing Sheets

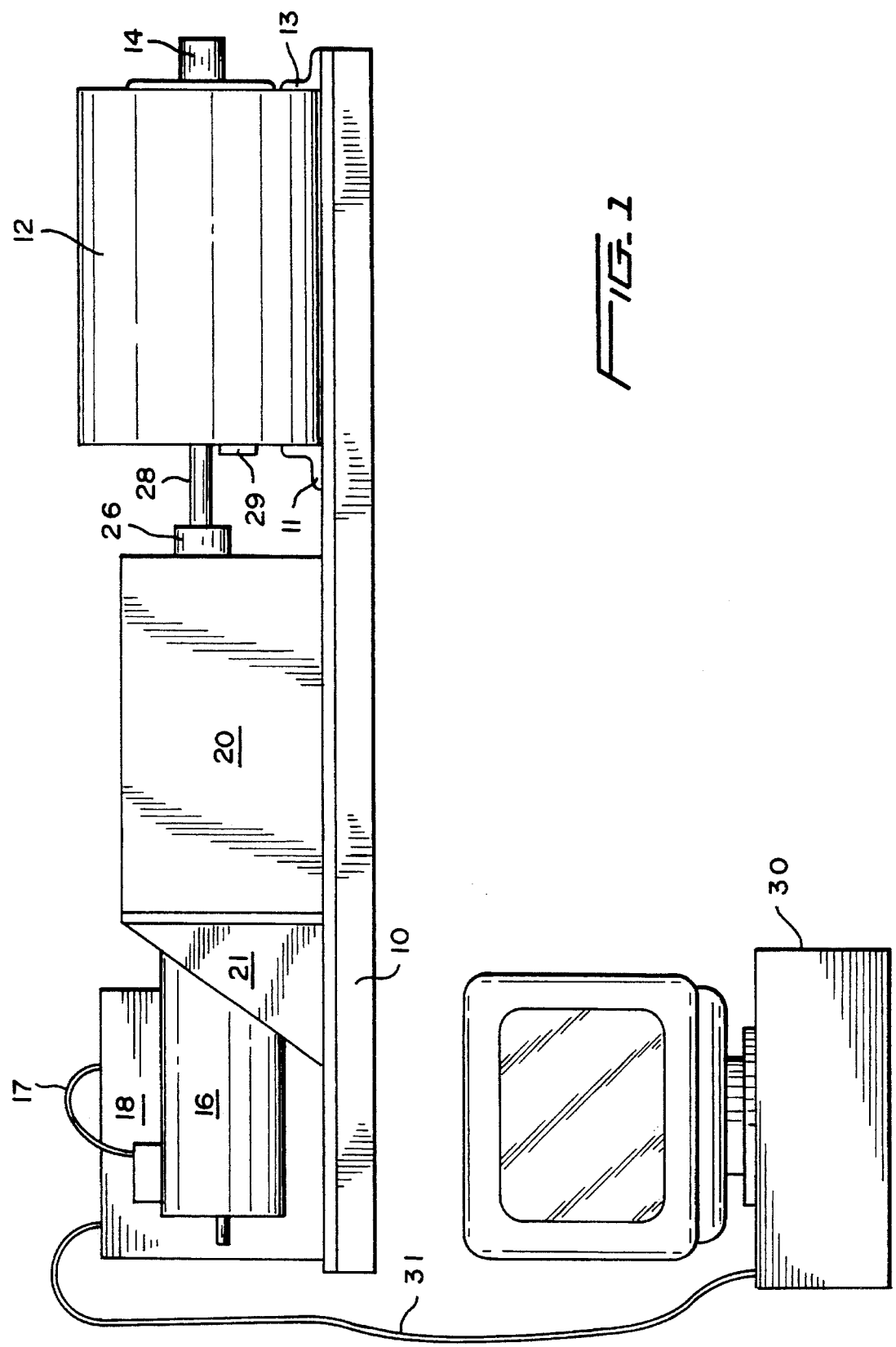

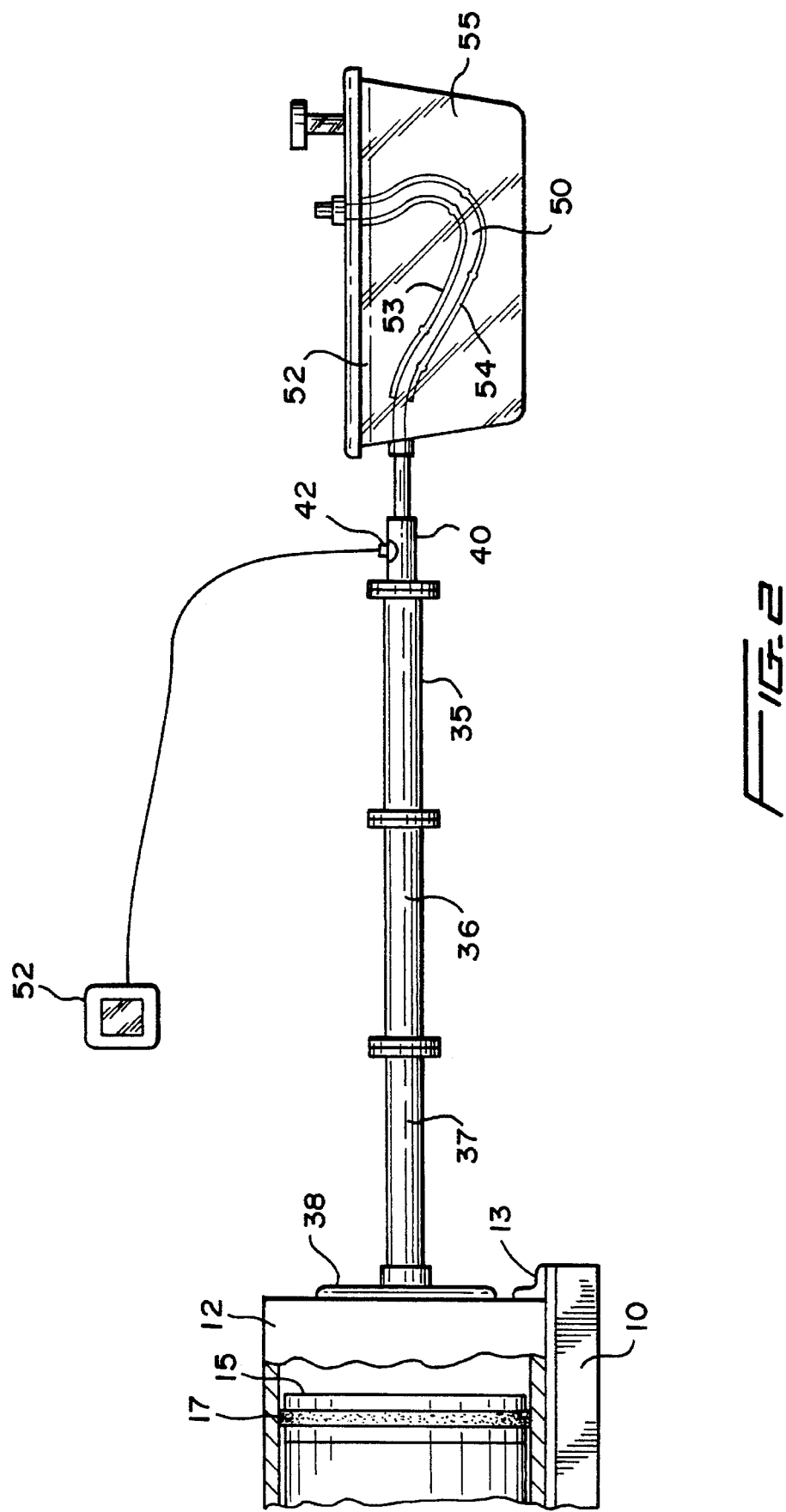

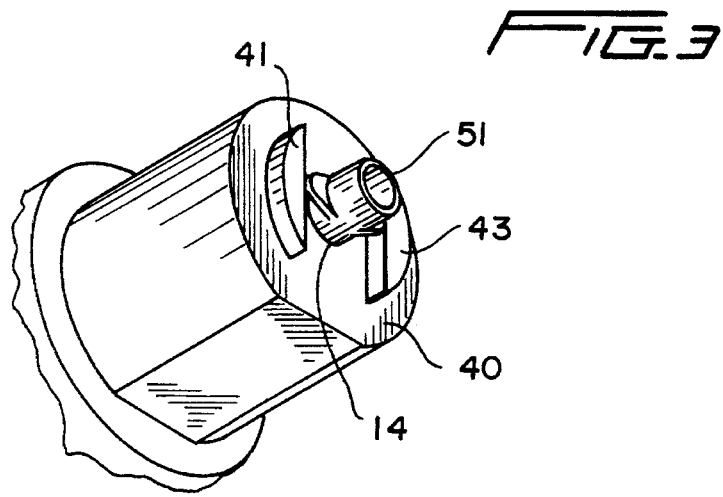
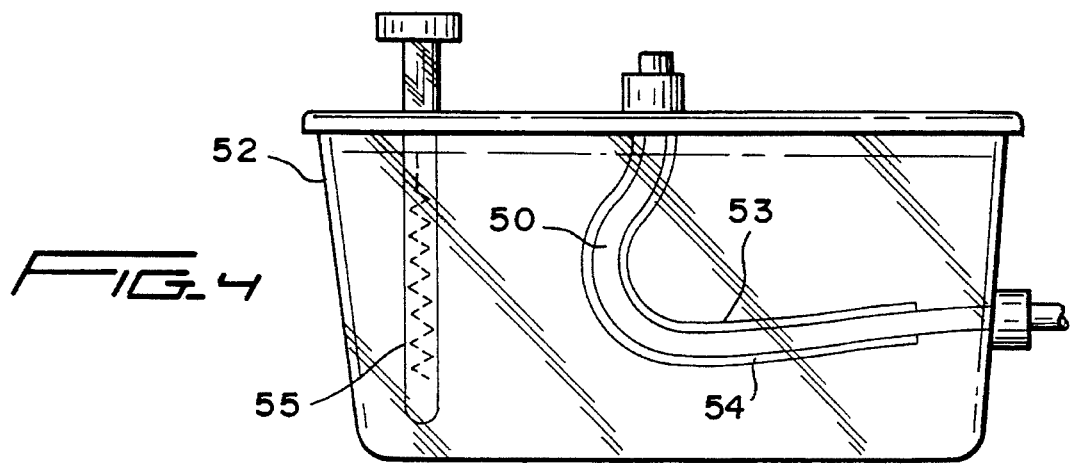
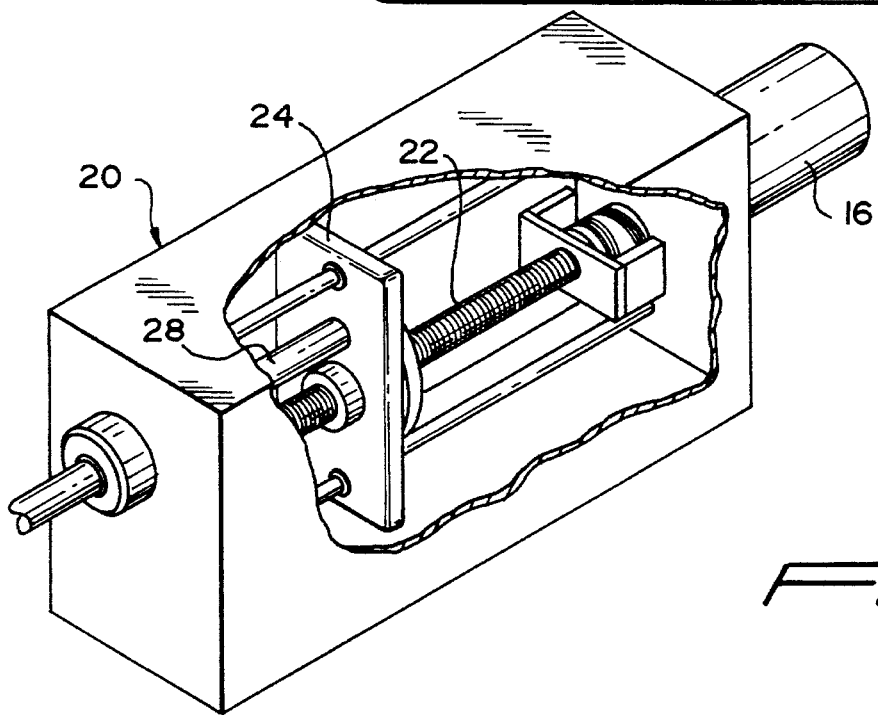

APPARATUS FOR TESTING POLYMONARY DEVICES

This application is a Continuation of application Ser. No. 08/029,615, filed Mar. 11, 1993, now abandoned.

The present invention relates to an apparatus for testing pulmonary devices and, more particularly, to a pulmonary wave generator for testing endotracheal tubes or the like under simulated conditions.

BACKGROUND OF THE INVENTION

Pulmonary devices, such as spirometers, peak flow meters, endotracheal tubes, connectors and the like are used in the testing and treatment of patients with pulmonary problems. A number of such devices, such as endotracheal tubes and connectors, are also used in the treatment of critically ill patients where any increase in the amount of work in breathing should be avoided.

Nevertheless, it has now been found that certain apparatus that is currently available have deficiencies that may have life-threatening consequences. For example, some of the materials selected for use in manufacturing endotracheal tubes are not heat stable in their physical characteristics at body temperatures and do not remain firm enough at those temperatures to retain their desired shapes while being inserted and while in place. Sometimes, a tube will collapse and/or kink, causing irritation if left in place and, more importantly, significantly reducing the rate of flow of air, oxygen, or mixture that can flow through the tube. The total volume of fluid flow per unit of time through a tube is given by Poiseuille's law as follows:

$$\frac{dV}{dT} = \frac{\pi}{8} \frac{R^4}{n} \frac{(P_1 - P_2)}{L}$$

where

V=volume of flow

R=radius of the tube $P_1$ and $P_2$=are the pressures at the respective ends of the tube n=viscosity of the flowing fluid L=the length of the tube From this equation, it is seen that any slight restriction in the radius R of the tube can have a significant reduction in the rate of flow through the tube since the radius is raised to the fourth power.

Similar problems exist in connection with endotracheal tube connectors for connecting an endotracheal tube to a source of oxygen or other gas. There are numerous such connectors on the market which do not minimize the work of breathing by reducing the negative pressure required to inhale a given volume of oxygen-enriched gas.

Accordingly, it is presently believed that there is a significant demand for a test apparatus for testing and evaluating pulmonary devices. Such apparatus would, for example, permit a hospital or doctor to readily determine which endotracheal tube and/or connector is optimal for a patient or patients. The physician or hospital could also screen devices, select the best product for their patients and assure themselves of accurate and repeatable tests and of a device that will not fail under in-use conditions.

In addition, it is presently believed that there is a demand for test apparatus which will measure flow resistance under simulated conditions with the direction of flow in two opposite directions, i.e., corresponding to the inhalation and exhalation of a patient. It is further believed that there is a demand for test apparatus which will produce or generate a particular pulmonary waveform such as any of 24 American Thoracic Society (ATS) Standard Pulmonary Waveforms.

It is also believed that an apparatus for testing pulmonary devices in accordance with the present invention will satisfy the aforementioned demands. Such apparatus are also relatively inexpensive to manufacture, durable, accurate, produce repeatable results and are easy to use.

SUMMARY OF THE INVENTION

In essence, an apparatus for testing pulmonary devices in accordance with the present invention comprises means for forcing a predetermined volume of air or gas through the pulmonary device in a first direction at a predetermined rate of flow and means for forcing or drawing a predetermined volume of gas through the pulmonary device in a second or opposite direction at a predetermined rate of flow. The apparatus also includes means for measuring the amount of work to force the gas through the device in each direction and means for recording the amount of work used in forcing the gas through the device in each direction. The apparatus, in accordance with a preferred embodiment of the invention, also includes means for controlling the gas flow to thereby produce a flow with a predetermined waveform.

A second embodiment of the invention is particularly applicable for testing endotracheal tubes and includes means for producing laminar and/or turbulent flow. In a preferred form of the second embodiment, a water bath, means for controlling the temperature of the water bath and means for conforming an endotracheal tube to the shape of a human trachea are provided so that the endotracheal tube can be tested under simulated conditions.

BRIEF DESCRIPTION OF THE DRAWINGS

FIG. 1 is a block diagram of an apparatus for testing pulmonary devices in accordance with a first embodiment of the invention;

FIG. 2 is a block diagram of a portion of an apparatus as used in testing endotracheal tubes;

FIG. 3 is a perspective view showing an air inlet/outlet portion of the device shown in FIG. 1 with an endotracheal tube connector mounted therein;

FIG. 4 is a side-elevational view of a water tank and means for positioning an endotracheal tube therein in accordance with one embodiment of the invention; and FIG. 5 is a perspective view of a rotary to linear motion mechanism for use in an apparatus according to the present invention.

DETAILED DESCRIPTION OF THE PREFERRED EMBODIMENTS OF THE INVENTION

The invention will now be described in connection with the accompanying drawings wherein like reference numerals have been used to indicate like parts.

An apparatus for testing pulmonary devices in accordance with a first embodiment of the invention is shown in FIG. 1. As shown therein, the device includes a base or frame 10 and an air cylinder 12 mounted thereon at one end thereof. The air cylinder 12 may, for example, be fixed to frame 10 by means of brackets 11 and 13. The air cylinder 12, which may be of conventional design, has a piston 15 (shown in FIG. 2)

reciprocally mounted therein. The piston 15 is in sliding sealing engagement with the air cylinder 12 by means of a piston ring 17.

The air cylinder 12, which is the equivalent of a large syringe, may, for example, have a maximum volume of about 12 liters. The cylinder 12 also defines an air inlet/outlet or relatively small opening 14 at one end thereof so that movement of the piston in a first direction, i.e., left to right in the illustration, will force the air out of the air cylinder 12 through the opening 14. Movement of the piston in the opposite direction will draw air through opening 14 and into air cylinder 12.

A motor 16 and motor driver 18 are mounted at the opposite end of frame 10 and are connected to one another by cable 17. A rotary-to-linear motion mechanism 20 is also fixed to frame 10 in between motor 16 and air cylinder 12 and held in place thereon by bracket 21. The rotary-to-linear motion mechanism 20 is operatively connected to motor 16 and converts rotary-motion to linear-motion in a customary manner.

As shown in FIG. 5, the rotary-to-linear motion mechanism 20 may include a threaded shaft 22 which is coupled to the shaft of motor 16. The shaft 22 is mounted in conventional bearings and when rotated in a first direction moves element 24 along a linear path. An element 24 of mechanism 20 is connected to a drive-shaft 28 which is in turn connected to the piston which is in air cylinder 12. Element 26 is a linear bearing for supporting piston drive shaft 28. In this manner, the rotation of motor 16 provides movement of the piston to thereby force air out of air cylinder 12 or draw air into cylinder 12 through opening 14.

A computer 30 is connected to the motor driver 18 by means of a conventional interface cable 31. Conventional computer software allows a user to control the motor speed and direction to deliver any of the 24 American Thoracic Society (ATS) Standard Pulmonary waveforms, other waveforms, waveforms of constant flow rate or a waveform with almost instantaneous peak flow rate and then exponentially decreasing flow rate or other waveform which the user may create. The programming for controlling motor speed and direction are well known to a programmer of ordinary skill in the art of providing computer aided motor controls and will vary in accordance with other design parameters such as the bore and stroke of the piston in the air cylinder and the ratio of rotary motion to linear motion provided by mechanism 20. The computer 30 may also be programmed in a conventional manner to reverse the direction of the piston when the stroke reaches it preprogrammed volume displacement.

In practice, it has been determined that a maximum volume of twelve liters is adequate for the air cylinder and that flow rates of up to twelve liters per second are adequate for testing most pulmonary devices of interest. Within these parameters, the apparatus disclosed herein can also be used to provide flow-volume loops (for minute ventilation testing) for testing spirometers, peak flow meters and other pulmonary equipment and devices. The apparatus can also be used to measure the amount of work done in driving air through tubing and/or orifices by continuously measuring the pressure, flow rate and time.

Under the user's direction, the system, in accordance with the present invention, i.e., the apparatus and software, reads a waveform file and calculates the necessary commands to direct a computer interface PC board (part of computer 30) to send the appropriate signals through interface cable 31 to the motor driver 18. The motor driver 18 then supplies the motor 16 with the appropriate power and drive signals to rotate at the correct speed and direction during each interval of time, for example, each 0.01 second. The apparatus also includes means such as motion limit switches and a "Home" switch (not shown). If, for example, there is an error while delivering a waveform, the motion limit switch 29 will stop the motor from rotating and possibly damaging the test apparatus or device under test.

A preferred embodiment of the invention will now be described in connection with FIG. 2 which illustrates a portion of the apparatus as used for testing an endotracheal tube or the like. As illustrated therein, three sections 35, 36 and 37 of pipe or tubing are connected together to provide a continuous smooth bore or passageway passing therethrough. The sections 35, 36 and 37 in the preferred embodiment each have an inside diameter of one inch to simulate the inside diameter of an average patient's trachea. Each section is also about 10" in length.

The section 37 is fixed at one end thereof to a face plate 38 of air cylinder 12 so that the opening 14 is concentric with the axis of sections 35, 36 and 37. An endpiece 40 is connected at the far end of section 37 concentrically therewith. The end piece 40 also has a bore which is identical to the bore of sections 35, 36 and 37 to thereby provide a relatively short extension thereof.

A pressure transducer 42 is fitted into end piece 40 for sensing the back pressure created when the pulmonary waveform generator apparatus forces air through a pulmonary device such as an endotracheal tube 50 which is connected to the end piece 40. The pressure transducer 42 is connected to a monitor 52 such as a strip chart recorder or other monitor or recording device for recording the pressure drop with respect to time.

The endotracheal tube 50 to be tested is immersed in a water container 52 and positioned or held in place in an in patient-use position by baffles 53 and 54. The container 52 and baffles are shown more clearly in FIG. 4. A heater-thermostat 55 heats and maintains the water at body temperature, i.e., between about 98° to 100° F.

With all three systems 35, 36 and 37 connected together, the endotracheal tube will receive laminar-flow air because the combined length of all three tubes is greater than 30 times the inside diameter of each identical tube. With two sections of tubing connected together, the endotracheal tube will receive a mixed flow of air, i.e. , somewhat turbulent, because the combined length of all three tubes is somewhat less than 30 times the inside diameter of each identical tube. With only one section of tubing connected to the output of the pulmonary waveform generator system, the endotracheal tube will receive turbulent air-flow because the length of one tube is much less than 30 times the inside diameter of each identical tube. With only the end piece and the pressure transducer attached to the output of the pulmonary waveform generator, the endotracheal tube will receive extremely turbulent air flow.

This testing set-up will allow the evaluation of endotracheal tubes in an anatomic configuration and environment. Thus, testing in this manner shows whether or not the endotracheal tube collapses or kinks when in a body-temperature water bath and held in a patient-use configuration. Also by monitoring the back pressure, using the pressure transducer, the amount of work to force air through the tube can be calculated, thus giving a close approximation of the work-of-breathing done by a patient with a similar endotracheal tube installed. This test set-up will also allow the evaluation and comparison of various types of endotracheal tubes.

A similar set up could be used to test other tubes and/or orifices for resistance to air flow under actual use conditions. And the amount of work to force air through the tube or orifice being tested can be calculated.

FIG. 3 shows the end piece 40 having a pair of flanges 41 and 43 which are adapted to hold an endotracheal tube connector 51 to end piece 40. The connector 51 is positioned to fit tightly into opening 14 so that air forced through the opening 14 will pass through the connector 51. In practice, an endotracheal tube connector may be tested alone or an endotracheal tube can be attached to the connector in a customary manner. In the latter case, the combination can be tested for optimal performance.

While the invention has been described in connection with one of its preferred embodiments, it should be understood that changes and modifications may be made without departing from the scope of the appended claims.

What is claimed is:

1. An apparatus for testing endotracheal tubes under simulated use conditions comprising means for forcing a predetermined volume of gas through the pulmonary device in a first direction at a predetermined rate of flow, means for forcing a predetermined volume of gas through the pulmonary device in a second direction at a predetermined rate of flow, means for measuring the amount of work to force the gas through the device in each direction and means for recording the amount of work expended in forcing the gas through the device in each direction, a water bath and means for controlling the temperature of said water bath to approximate that of a human patient and means within said water tank for conforming the endotracheal tube to the shape of a human trachea so that the endotracheal tube is tested under simulated conditions.

2. An apparatus for testing endotracheal tubes according to claim 1 which includes means for controlling the rate of flow of the gas to produce a flow with a predetermined waveform.

3. The apparatus for testing endotracheal tubes according to claim 2 which includes a plurality of rigid cylindrical tubes connected together and having a combined length to diameter ratio which exceeds 30 to 1 for connecting the endotracheal tube to the opening in said air cylinder.

4. A method for testing pulmonary devices comprising the steps of:

forcing a predetermined volume of gas through the pulmonary device in a first direction at a predetermined rate of flow, forcing a predetermined volume of gas through the device in an opposite direction at a predetermined rate of flow, measuring the amount of work to force the gas through the device in each direction, and recording the amount of work to force the gas through the device in each direction.

5. A method for testing pulmonary devices in accordance with claim 4 which includes the step of immersing the device in a water bath and controlling the temperature of the bath at a temperature of a human patient during the testing procedure.

6. A method for testing pulmonary devices comprising the step of providing an endotracheal tube and immersing the endotracheal tube in a water bath and controlling the temperature of the bath at a temperature of a human patient during the testing procedure and the step of positioning the endotracheal tube in the shape of a human trachea while immersed in the heated water bath so that the test is performed under simulated conditions; the method further comprising the steps of forcing a predetermined volume of gas through the pulmonary device in a first direction at a predetermined rate of flow, forcing a predetermined volume of gas through the device in an opposite direction at a predetermined rate of flow, measuring the amount of work to force the gas through the device in each direction, and recording the amount of work to force the gas through the device in each direction.

* * * * *

UNITED STATES PATENT AND TRADEMARK OFFICE
CERTIFICATE OF CORRECTION

PATENT NO. : 5,473,954

DATED : December 12, 1995

INVENTOR(S) : HOYT et al.

It is certified that error appears in the above-indentified patent and that said Letters Patent is hereby corrected as shown below:

Title page,
Item [54], "POLYMONARY" should read --PULMONARY--.

Column 1, line 1, "POLYMONARY" should read --PULMONARY--.

Signed and Sealed this

Twelfth Day of March, 1996

Attest:

BRUCE LEHMAN

*Attesting Officer*  *Commissioner of Patents and Trademarks*